US008527043B2

(12) United States Patent
Dupelle et al.

(10) Patent No.: US 8,527,043 B2
(45) Date of Patent: Sep. 3, 2013

(54) SYSTEMS AND METHODS FOR ENHANCED VENOUS RETURN FLOW DURING CARDIAC EVENT

(75) Inventors: Michael R. Dupelle, North Attleboro, MA (US); Mary Ann Dupelle, legal representative, North Attleboro, MA (US); Sheldon S. White, Brookline, MA (US)

(73) Assignee: Zoll Medical Corporation, Chelmsford, MA (US)

( * ) Notice: Subject to any disclaimer, the term of this patent is extended or adjusted under 35 U.S.C. 154(b) by 186 days.

(21) Appl. No.: 13/117,333

(22) Filed: May 27, 2011

(65) Prior Publication Data

US 2011/0313482 A1 Dec. 22, 2011

Related U.S. Application Data

(60) Provisional application No. 61/349,456, filed on May 28, 2010.

(51) Int. Cl.
*A61N 1/04* (2006.01)

(52) U.S. Cl.
USPC .............................. 607/3; 600/481

(58) Field of Classification Search
USPC ............. 600/16–18, 301, 481, 485, 508, 509; 607/3, 48; 601/41, 43, 44, 148, 150, 151
See application file for complete search history.

(56) References Cited

U.S. PATENT DOCUMENTS

| 5,000,164 | A | 3/1991 | Cooper |
| 5,149,321 | A | 9/1992 | Klatz et al. |
| 5,284,135 | A | 2/1994 | Lopin |
| 5,330,526 | A | 7/1994 | Fincke et al. |
| 5,339,526 | A | 8/1994 | Everts |
| 5,370,603 | A | 12/1994 | Newman |
| 5,458,562 | A | 10/1995 | Cooper |
| 5,485,562 | A | 1/1996 | Narayanaswami |
| 5,514,079 | A | 5/1996 | Dillon |
| 5,674,262 | A | 10/1997 | Tumey |
| 6,010,470 | A | 1/2000 | Albery et al. |
| 6,096,063 | A | 8/2000 | Lopin et al. |
| 6,312,399 | B1 | 11/2001 | Lurie et al. |
| 6,575,914 | B2 | 6/2003 | Rock et al. |
| 6,827,695 | B2 | 12/2004 | Plazzolo et al. |
| 6,865,413 | B2 | 3/2005 | Halperin et al. |
| 7,074,199 | B2 | 7/2006 | Halperin et al. |
| 7,108,665 | B2 | 9/2006 | Halperin et al. |
| 7,118,542 | B2 | 10/2006 | Palazzolo et al. |

(Continued)

FOREIGN PATENT DOCUMENTS

JP 2005052223 A 3/2005

OTHER PUBLICATIONS

International Search Report from corresponding PCT Application No. PCT/US2011/38362, dated Oct. 3, 2011.
Pouran D. Faghri, et al., Venous Hemodynamics of the Lower Extremities in Response to Electrical Stimulation, Arch Phys Med Rehabil vol. 79, Jul. 1998, pp. 842-848.

(Continued)

*Primary Examiner* — Brian T Gedeon
(74) *Attorney, Agent, or Firm* — Lando & Anastasi, LLP (57) ABSTRACT

Systems and methods of enhancing cardiopulmonary circulation in a subject during resuscitation are provided. A signal is received responsive to an induced heart compression that is applied to the subject, for example during ventricular fibrillation, an asystolic condition, or cardiac arrest. Responsive to receipt of the signal, a muscle distal subject's heart is electrically stimulated to contract and expel blood into the venous blood flow toward a heart of the subject.

30 Claims, 7 Drawing Sheets

(56) References Cited

U.S. PATENT DOCUMENTS

| | | |
|---|---|---|
| 7,122,014 B2 | 10/2006 | Palazzolo et al. |
| 7,220,235 B2 | 5/2007 | Geheb et al. |
| 7,245,974 B2 | 7/2007 | Dupelle et al. |
| 7,277,751 B2 | 10/2007 | Dupelle et al. |
| 7,295,871 B2 | 11/2007 | Halperin et al. |
| 7,310,553 B2 | 12/2007 | Freeman |
| 7,476,206 B2 | 1/2009 | Palazzolo et al. |
| 7,488,293 B2 | 2/2009 | Marcovecchio et al. |
| 7,565,194 B2 | 7/2009 | Tan et al. |
| 7,645,247 B2 | 1/2010 | Paradis |
| 2004/0030270 A1 | 2/2004 | Johnson |
| 2004/0254624 A1 | 12/2004 | Johnson |
| 2006/0036292 A1 | 2/2006 | Smith et al. |
| 2006/0089574 A1 | 4/2006 | Paradis |
| 2006/0178706 A1 | 8/2006 | Lisogurski et al. |
| 2006/0270952 A1 | 11/2006 | Freeman et al. |
| 2007/0270917 A1 | 11/2007 | Nachum |
| 2008/0319359 A1 | 12/2008 | Moomiaie-Qajar et al. |

OTHER PUBLICATIONS

G.M. Lyons, et al., The Effect of Electrical Stimulation of the Calf Muscle and Compression Stocking on Venous Blood Flow Velocity, Eur J Vasc Endovasc Surg vol. 23, Jun. 2002, pp. 564-566.

Jacqui Raymond, et al., Cardiovascular Responses to an Orthostatic Challene and Electrical-Stimulation-Induced Leg Muscle Contractions in Individuals With Paraplegia, Eur J Apl Physiol (1999) 80: 205-212.

Babbs;CPR Techniques that Combine Chest and Abdominal Compression and decompression; Circulation 1999: 2146-2152.

Xu, et al; Optimizing Sequence for Enhanced Counter-Pulsation during AEI-CPR based on Genetic Algorithm; 2008 IEEE International Workshop on Modeling, Simulation, and Optimization.

Perlovitch et al; Inspiratory muscles experience fatigue faster than the calf muscles during treadmill marching; 2007 p. 61-68; Respiratory Physiology & Neurobiology 156.

Faghri et al; Electrical Stimulation-induced contraction to reduce blood stasis during arthoplasty; IEEE Transactions on Rehabilitation Engineering, vol. 5, No. 1, Mar. 1997.

SYSTEMS AND METHODS FOR ENHANCED VENOUS RETURN FLOW DURING CARDIAC EVENT

CROSS REFERENCE TO RELATED APPLICATIONS

This application claims priority under 35 U.S.C. 119(e) to U.S. Provisional Application Ser. No. 61/349,456 titled "Systems and Methods for Enhanced Venous Return Flow During Cardiac Event," filed May 28, 2010, which is incorporated herein by reference in its entirety.

BACKGROUND OF THE INVENTION

1. Field of Invention

The present invention is generally directed to cardiopulmonary circulation, and more specifically, to systems and methods that can enhance cardiopulmonary circulation during ventricular fibrillation, an asystolic condition, or sudden cardiac arrest.

2. Discussion of Related Art

Cardiac arrest and other cardiac health ailments are a major cause of death worldwide. Various resuscitation efforts aim to maintain the body's circulatory and respiratory systems during cardiac arrest in an attempt to save the life of the victim. These efforts have a limited success rate, and cardiac arrest, among other conditions, continues to claim the lives of victims.

SUMMARY OF THE INVENTION

Aspects and embodiments of the present invention are directed to systems and methods of enhancing cardiopulmonary circulation in a subject. To increase venous blood flow toward the subject's heart during, for example, resuscitation efforts, controlled contractions of a muscle located remotely from the heart are induced. These controlled contractions increase the amount of blood in the venous blood flow toward the heart, enabling more blood to enter the subject's chest cavity, heart, and lungs during an expansion or relaxation phase of the heart.

At least one aspect is directed to a method of enhancing cardiopulmonary circulation in a subject. The method includes an act of receiving a signal responsive to an induced heart compression applied to the subject. The method further includes an act of electrically stimulating, responsive to receipt of the signal, a muscle that is located distal to a chest cavity and abdomen of the subject to contract and increase venous blood flow toward a heart of the subject.

In various embodiments, the muscle is electrically stimulated, for example using energy drawn from the power source of a cardiopulmonary resuscitation device. In one embodiment, blood is expelled from the muscle into a venous blood flow toward the chest cavity during a relaxation phase of the subject's heart muscle subsequent to the induced heart compression. In an alternate embodiment, blood is expelled from the muscle into a venous blood flow toward the chest cavity during a compression phase of the subject's heart muscle. In one embodiment, the signal is received at a rate of 70 to 110 times per minute, and the muscle is electrically stimulated at a rate of one to five times per minute.

In one embodiment, a first portion of the muscle is stimulated to contract at a first time, and a second portion of the muscle is stimulated to contract at a second time. Further, the muscle can be stimulated in response to a determination that the muscle in engorged with the threshold amount of blood. In some embodiments, the stimulation electrode induces contraction of the muscle upon expiration of a determined time period. This stimulation may occur during either the compression phase of the heart or the relaxation phase of the heart. The controller can issue an instruction for the heart compression to be induced manually or mechanically during at least one of ventricular fibrillation, an asystolic condition, and cardiac arrest.

At least one other aspect is directed to a stimulation device to enhance cardiopulmonary circulation during resuscitation. The stimulation device includes a stimulation electrode configured for placement onto a limb of the subject. The stimulation device also includes a controller that is communicatively coupled to the stimulation electrode. The controller receives a signal indicative of an induced heart compression applied to a heart of the subject. Responsive to receipt of the signal, the controller directs the stimulation electrode to induce contraction of a muscle in the limb of the subject to force blood from the muscle and into a venous blood flow toward the heart.

In some embodiments, the controller receives the signal indicative of a stimulated heart compression from a cardiopulmonary resuscitation device that may include a power source that powers both the stimulation device and the cardiopulmonary resuscitation device. The controller can receive the signal indicative of an induced heart compression at a rate of 70 to 110 times per minute and can direct the stimulation electrode to induce contraction of the muscle at a rate of one to five times per minute. The controller can also determine an amount of blood present in the muscle and direct the stimulation electrode to induce contraction of the muscle when the amount of blood present in the muscle is greater than a threshold amount of blood. In various embodiments, the stimulation electrode is disposed in a housing having an incomplete cylinder shape, and the stimulation electrode may include a conductive plate affixed to an inner surface of the housing.

At least one other aspect is directed to a method of facilitating care of a subject. The method includes an act of providing a stimulation device to enhance cardiopulmonary circulation in a subject. The stimulation device includes a stimulation electrode configured for placement onto a limb of the subject and a controller communicatively coupled to the stimulation electrode and configured to receive a signal indicative of an induced heart compression applied to a heart of the subject. Responsive to receipt of the signal, the controller directs the stimulation electrode to induce contraction of a muscle in the limb of the subject to force blood from the muscle and into a venous blood flow toward the heart. In one embodiment, the method further includes an act of providing instructions to operate the stimulation device, the instructions including at least one instruction directing a user to place the stimulation electrode on the limb of the subject.

These aspects and embodiments are discussed in detail below. Both the foregoing information and the following detailed description are illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain the described and claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

The systems and methods described herein are not limited in their application to the details of construction and the arrangement of components set forth in the description or illustrated in the drawings. The systems and methods are capable of other embodiments and of being practiced or of being carried out in various ways. Also, the phraseology and terminology used herein is for the purpose of description and should not be regarded as limiting. The use of "including," "comprising," "having," "containing," "involving," and variations thereof, is meant to encompass the items listed thereafter, equivalents thereof, and additional items, as well as alternate embodiments consisting of the items listed thereafter exclusively.

Various aspects and embodiments are directed to systems and methods of enhancing cardiopulmonary circulation in a subject during resuscitation efforts such as cardiopulmonary resuscitation. Venous blood flow to the heart can be disrupted during sudden cardiac arrest. During such an event, cardiopulmonary resuscitation efforts induce periodic heart or chest compressions, for example by electrical stimulation or chest compressions, to pump blood through the circulatory system. This blood flow prolongs organ function increasing the probability that the subject will survive, and decreasing the risk of permanent health damage.

Increasing the volume of venous return blood flow toward the chest cavity and heart increases overall circulation and increases the amount of blood that is oxygenated during resuscitation efforts. Stimulating certain muscles such as the calf muscle to contract causes those muscles to force blood toward the heart and lungs, where it is oxygenated. This complements the venous blood flow created by the heart compressions alone. Synchronizing the stimulated muscle contractions with the induced heart compressions increases venous blood flow toward the heart, and facilitates filling of the heart with venous blood for oxygenization.

Figure 1:
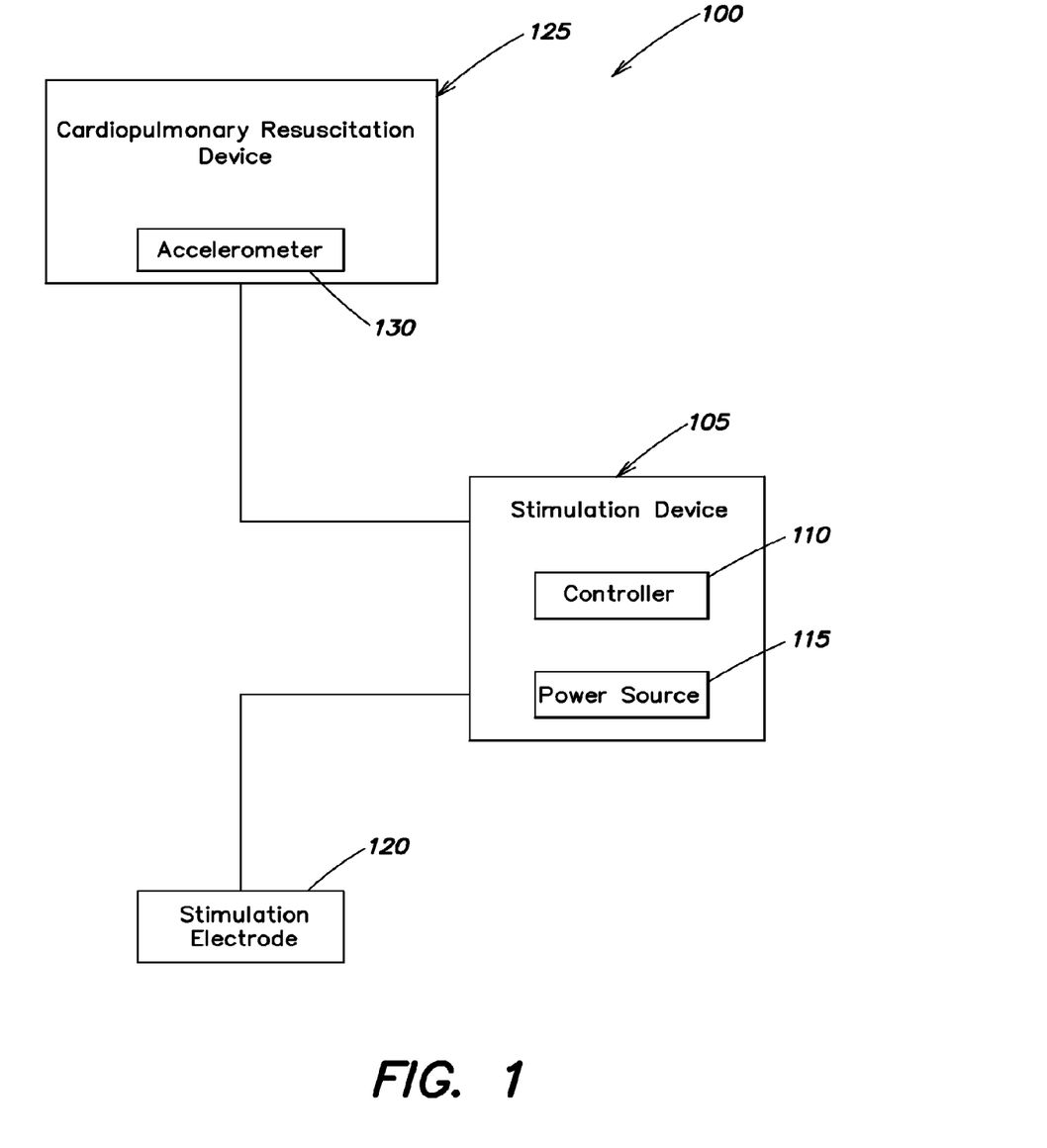
FIG. 1 is a functional block diagram of a system to enhance circulation in accordance with an embodiment.

FIG. 1 is a functional block diagram of a system 100 to enhance circulation in accordance with an embodiment. System 100 includes at least one stimulation device 105 that is associated with at least one stimulation electrode 120 and at least one associated cardiopulmonary resuscitation device 125. The stimulation device 105 includes at least one controller 110 that directs operations performed by stimulation device 105 and at least one power source 115. Cardiopulmonary resuscitation device 125 includes an accelerometer 130 or force sensor that is capable of detecting chest compressions. An exemplary cardiopulmonary resuscitation device is described, for example, in U.S. Pat. No. 7,310,553, which is incorporated herein by reference in its entirety.

As illustrated in FIG. 1, controller 110 and power source 115 are part of stimulation device 105, with power source 115 providing electrical power to both stimulation electrode 120 and cardiopulmonary resuscitation device 125. Other configurations are possible. For example, controller 110 and power source 115 can be separate from stimulation device 105. In some embodiments, one or both of stimulation electrode 120 and cardiopulmonary resuscitation device 125 have separate controllers 110 and power sources 115, the same controller 110 and separate power sources 115, or separate controllers 110 and the same power source 115. In one embodiment, power source 115 powers stimulation electrode 120 and is part of a stand-alone cardiopulmonary resuscitation device 125. In addition to powering stimulation electrode 120, power source 115 can be part of a transcutaneous external pacing unit that provides electrical pulses of about 70-90 mA and 20V to control the subject's heart. In one embodiment, power source 115 is part of a transcutaneous electrical nerve stimulation (TENS) unit. Power source 115 can also be part of an automatic external defibrillator unit that can provide a more than 1000V charge to the subject. Power source 115 may include batteries or other power supplies, including AC power supplies and uninterruptible power supplies.

In one embodiment, one or more of stimulation device 105, power source 115, stimulation electrode 120, and cardiopulmonary resuscitation device 125 includes dedicated control logic devices that collectively constitute controller 110. Such dedicated control logic can include programmable logic devices and arrays, application specific integrated circuits, hardware and software combinations, general purpose processors and dedicated controllers, for example. Further, each of stimulation device 105, and cardiopulmonary resuscitation device 125 may include graphical user interfaces or other interfaces to provide output information and receive input information from a user. In one embodiment, stimulation device 105 includes stimulation electrode 120.

In one embodiment, using for example transcutaneous electrical nerve stimulation, stimulation electrode 120 stimulates a muscle (e.g., a calf muscle) to contract in synchronization with the compression/decompression strokes associated with cardiopulmonary resuscitation device 125, increasing return blood flow from, for example, the legs to the heart during cardiopulmonary resuscitation. For example, stimulation electrode 120 can include a pair of electrodes for placement on the subject at different portions of a muscle. In this example, the pair of stimulation electrodes 120 and the muscle form at least part of a circuit so that current follows a path between the pair of stimulation electrodes 120 and through the muscle, causing muscle stimulation. Other configurations are possible, such as an array of stimulation electrodes 120 configured to form at least part of one electrical circuit that includes at least a portion of one muscle between at least two stimulation electrodes 120. In one embodiment, different pairs of stimulation electrodes 120 stimulate different muscles, either simultaneously or sequentially.

In one embodiment, during an event such as sudden cardiac arrest, ventricular fibrillation, or an asystolic condition where cardiopulmonary resuscitation is desired, cardiopulmonary resuscitation device 125 may provide instructions to a rescuer regarding the rate and depth of chest compressions. These instructions may be in accordance with American Heart Association (AHA) or other health agency guidelines. Chest compressions associated with cardiopulmonary resuscitation device 125 mechanically support circulation by maintaining blood circulation and oxygen delivery until the heart is restarted. To create blood flow through the heart based on chest compressions and expansions, the chest is released after a chest compression to create negative thoracic pressure in the chest during expansion. This facilitates venous filling of the heart and continued blood flow upon the next chest compression.

The volume of oxygen depleted return blood flow to the heart and lungs during the relaxation or expansion phase of cardiopulmonary resuscitation is augmented by contracting a muscle such as a leg muscle, or other muscle distal to the subject's chest cavity and abdomen. This distal muscle contraction expels blood from the muscle and forces it toward the chest cavity. This provides a positive pressure to venous blood flow at a point outside the subject's chest cavity, complementing any negative thoracic pressure created during heart relaxation or chest expansion and increasing venous blood flow toward the heart. For example, stimulation electrode 120 may induce contraction of a muscle distal to the subject's heart, chest cavity, and abdomen to force blood from that muscle toward the chest cavity, where the blood forced from the muscle eventually enters the chest cavity during a negative thoracic pressure phase of the chest cavity.

In one embodiment, system 100 or its component devices such as stimulation device 105 and stimulation electrode 120 are operated by rescuers such as trained medical personnel, first responders, or civilian good Samaritans. For example, stimulation electrode 120 can be placed onto a subject's limb. In this example, stimulation device 105 receives a signal indicative of an induced heart compression. There are a variety of ways in which the heart compression can be induced. For example, heart compressions can be induced at least in part by a mechanical chest compression device. Such a device may be human powered, pneumatically driven, or driven by a motor, as well as combinations thereof. In one embodiment, heart compression is induced by use of a non-invasive cardiac support pump such as the AutoPulse® pump manufactured by the Zoll Medical Corporation of Chelmsford Mass.

In some embodiments, a rescuer may induce heart compressions via chest compressions during cardiopulmonary resuscitation. In some embodiments, cardiopulmonary resuscitation device 125 is placed, for example, on the patient's chest generally proximate to the heart, and instructs the rescuer to take some action (e.g., chest compressions) that induce at least one heart compression by providing an audio or visual signal to the rescuer. In one embodiment, controller 110 of stimulation device 105 instructs cardiopulmonary resuscitation device 125 to induce a heart compression either directly or with rescuer intervention.

In one embodiment, cardiopulmonary resuscitation device 125 provides a signal to stimulation device 105 indicative of an induced heart compression. For example, a force sensor or an accelerometer associated with cardiopulmonary resuscitation device 125 can detect a chest compression that is of sufficient velocity or depth to induce a heart compression and cardiopulmonary resuscitation device 125 can provide this information to stimulation device 105. The rescuer or rescuers may also provide this signal directly to stimulation device 105 when the rescuer determines that at least one heart compression has been induced. In one embodiment, this signal indicates an induced heart compression of a patient during sudden cardiac arrest or ventricular fibrillation where there is no electrocardiograph (EKG or ECG) signal during resuscitation efforts.

In one embodiment, stimulation device 105 receives the signal indicative of an induced heart compression. Responsive to this signal, stimulation device 105 and controller 110 direct stimulation electrode 120 to electrically induce contraction of a muscle of the subject that is located distal to the subject's heart, for example, a leg muscle such as the calf. The contraction induced by stimulation electrode 120 expels blood through the muscle and toward the subject's heart, increasing the overall venous return blood flow that can be oxygenated during continued circulation through the subject. It is appreciated that the cardiovascular system of human subjects is closed, such that the blood expelled out of or through the subject's muscles remains in the subject's network of blood vessels.

In one embodiment, responsive to an induced heart compression, controller 110 determines when to induce contraction of another muscle that is not the heart muscle. For example, controller 110 can determine a time period that begins when the induced heart compression occurred, and can direct stimulation electrode 120 to induce the muscle to contract upon expiration of that time period. In one embodiment, controller 110 receives the signal indicative of induced heart compression from cardiopulmonary resuscitation device 125 and, based at least in part on information provided by the signal, determines when to direct stimulation electrode 120 to induce contraction of its associated muscle. Responsive to instructions received from stimulation device 105 via controller 110, stimulation electrode 120 may apply a signal such as an electric current or pulse to the subject to induce contraction of the muscle.

The ratio between induced heart compression attributable to cardiopulmonary resuscitation device 125 and induced muscle contractions attributable to stimulation electrode 120 may vary. For example, cardiopulmonary resuscitation device 125 can directly (e.g., electrically) or indirectly (e.g., via instructions to a rescuer) induce heart compressions at a rate of 70 to 110 times per minute, and stimulation electrode 120 can directly or indirectly induce muscle contractions at a rate of one to five times per minute. The rate of muscle contractions induced by stimulation electrode 120 to induced heart compressions may vary, for example, based on the size of the subject or the perceived severity of the sudden cardiac arrest or ventricular fibrillation, from once for every 5 induced heart compressions to once for every 100 induced heart compressions. These ratios are examples, and others within and beyond these ranges are possible.

In one embodiment where accelerometer 130 identifies induced heart compression, controller 110 can identify or approximate the velocity, rate, or depth of the chest compressions. This information can also be communicated to controller 110 automatically using control logic, by a rescuer, or by the subject using an interface of stimulation device 105 or cardiopulmonary resuscitation device 125. This information can be used by controller 110 to determine when to instruct stimulation electrode 120 to induce muscle contractions. In one embodiment, controller 110 may use an impedance measurement across the muscle to determine approximately how much blood is present in the muscle. Based on the measured impedance, controller 110 can determine that the muscle is engorged with a threshold amount of blood, e.g., at least 100 mL for a larger muscle such as a calf muscle, and can instruct stimulation electrode 120 to induce contraction of that muscle. Some muscles, such as smaller limb muscles, have threshold amounts of blood that are less than 100 mL.

Figure 2:
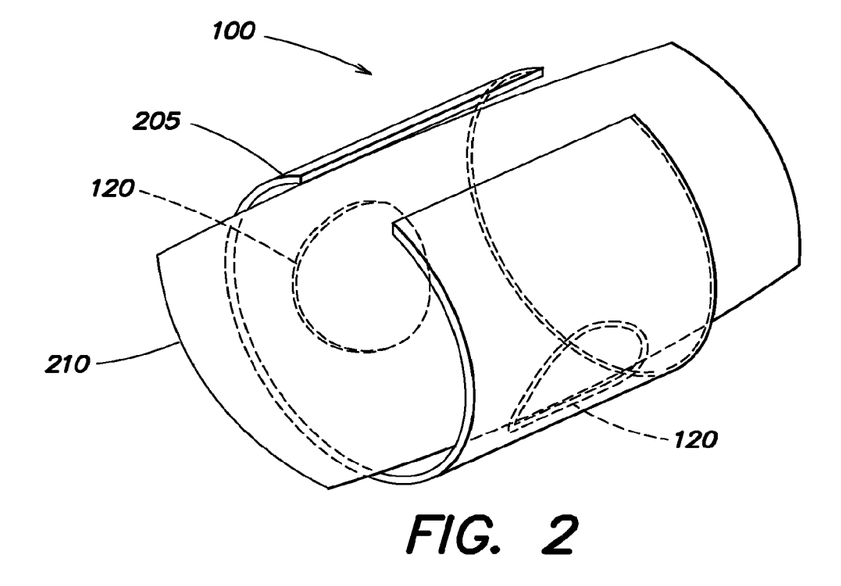
FIG. 2 is a partial perspective view depicting stimulation electrodes in accordance with an embodiment.

FIG. 2 is a partial perspective view of a system to enhance circulation and depicts a stimulation electrode 120 in accordance with an embodiment. FIG. 2 depicts two stimulation electrodes 120 located in a housing 205 that is constructed to be placed about a limb 210 of the subject. In some embodiments, housing 205 includes one, two, or more than two stimulation electrodes 120. In one embodiment, stimulation electrodes 120 need not be disposed in any housing and can be free standing electrodes that are in electrical contact with the subject's body. In one embodiment, housing 205 has the shape of a sleeve configured for placement around limb 210, and housing 205 can be made of a flexible material, such as nylon or other polymers. Housing 205 can also be made of cotton, cloth, rubber, or other synthetic or non-synthetic materials. In one embodiment, housing 205 has a generally fixed, rigid shape and includes hard plastic material. In one embodiment, housing 205 is a mechanical device having hinges or spring elements to form a desired shape for rapid placement onto a limb and urge stimulation electrodes 120 into good electrical contact with the subject's body. Housing 205 can be manipulated by the rescuer into a generally cylindrical shape about limb 210, as well as other portions of the subject's body.

In one embodiment, housing 205 is configured for rapid placement onto a subject. With reference to FIG. 2, housing 205 can form an incomplete cylinder, so that the two opposite ends do not touch or overlap when wrapped around limb 210. Other configurations are possible. For example, housing 205 can completely wrap around a portion of a limb as a sleeve and can be secured in this configuration by hook and loop fasteners, adhesives, buttons, clips, zippers, strings that are tied together, elastics, and other fasteners. In one embodiment, housing 205 is constructed and arranged for quick placement by a rescuer about a limb or other part of the subject's body. For example, where the subject is unresponsive, housing 205 with its open longitudinal ends can be arranged about the subject's lower leg in a matter of a few seconds and does not require precise fitting or extensive movement of the subject. In some embodiments, housing 205 includes a ribbed, elasticized, or reinforced band.

In one embodiment, stimulation electrodes 120 are integral to housing 205 and affixed in a generally permanent manner. For example, stimulation electrodes 120 can be sewn into an inner surface of housing 205, facing the subject, when housing 205 is a nylon sleeve, or affixed to an inner surface of housing 205 when housing 205 is a rigid plastic case. In other embodiments, housing 205 is constructed to facilitate insertion and removal of stimulation electrodes 120, for example, by having a plurality of pockets or sleeves for insertion and removal of stimulation electrodes 120. In this example, buttons, elastics, hook and loop fasteners and the like may be used to affix stimulation electrodes 120 into housing 205, allowing a single housing 205 to accommodate one or more stimulation electrodes 120 having different sizes, shapes, weights, and electrical characteristics. In one embodiment, housing 205 is constructed to accommodate one or more of controller 110, power source 115, and devices for communication between any of stimulation electrodes 120, stimulation device 105, and cardiopulmonary resuscitation device 125.

In one embodiment, stimulation electrodes 120 include electrically conductive plates that are exposed by housing 205 so that they contact the subject when housing 205 is placed onto part of the subject's body. In some embodiments, stimulation electrodes 120 trigger muscle contraction directly, e.g., via contact between the subject's skin and the conductive plates of stimulation electrodes 120; or indirectly, e.g., with intervening elements to facilitate conductivity, or intervening elements such as the subject's clothes, part of housing 205, or a protective material inserted between the subject's skin and stimulation electrode 120. For example, a conductive fluid such as a gel or a conductive solid such as a paste can be applied to the conductive plates of stimulation electrodes 120, or to the subject's body at the location where stimulation electrodes 120 are brought into contact with the subject (e.g., a limb). For example, gel may be placed in a series of packs disposed on stimulation electrodes 120. In this example, these gel packs can burst when applied to the subject or when stimulation electrodes 120 are activated, dispersing the gel between the subject and stimulation electrodes 120. In one embodiment, a conductive hydrogel is applied to stimulation electrode 120 substantially or fully covering the surface of stimulation electrode 120 that is applied to the subject's skin. In one embodiment, stimulation electrodes 120 include projections that penetrate the subject's clothes to contact the subject's skin.

In one embodiment, stimulation electrode 120 is located proximate to a muscle and provides an electrical current or voltage to the subject sufficient to induce contraction of that muscle. For example, at a time determined by controller 110, stimulation device 105 can activate, so that current follows a path from stimulation device 105 to stimulation electrode 120. The current passes to the subject and stimulates muscle contraction. In this example, stimulation device 105 and stimulation electrode 120 may be part of a transcutaneous electrical nerve stimulation unit.

The source of the current applied by stimulation electrode 120 to the subject can be provided by power source 115, which may be a separate power source, or a power source included within stimulation device 105, housing 205, or cardiopulmonary resuscitation device 125. In one embodiment, stimulation electrode 120 applies 20-25mA of current to the subject to stimulate muscle contraction. Stimulation electrode 120 can apply current to the muscle to stimulate the muscle directly, or can apply current to nerves or tissue associated with the muscle that in turn stimulate muscle contraction. In one embodiment, electrical energy initiates contraction of a muscle of the subject during a cardiac event, in the absence of inflatable therapeutic devices such as a pressurized cuff or sock that may be used to improve circulation in patients having poor circulation, but a normal cardiac rhythm.

In one embodiment, a first pair of stimulation electrodes 120 can be placed proximate to a first muscle and a second pair of stimulation electrodes 120 can be placed proximate to a second muscle. The first and second muscles can be part of the same muscle group, such as the gastrocnemius and soleus muscles of the calf, muscles of different muscle groups, different muscles of the same limb, the same muscle of different limbs, (e.g., the gastrocnemius calf muscle of both the left and right leg), or muscles of other body parts. In some embodiments, a plurality of stimulation electrodes 120 can stimulate different portions of the same muscle at the same time, or at different times.

In one embodiment, two stimulation electrodes 120 are placed proximate to a muscle so that, when stimulated, current follows a path between the two stimulation electrodes 120 and through the muscle. This generally forms a closed circuit that includes power source 115, the two stimulation electrodes 120, and the muscle being stimulated. In this illustrative embodiment, additional stimulation electrodes 120 can be placed proximate to different muscles for additional stimulation.

In one embodiment, responsive to a signal indicating an induced heart compression, controller 110 independently controls the first and second stimulation electrodes 120 to stimulate contraction of their associated muscles in a complementary fashion that enhances venous blood flow toward the heart. For example, under the direction of controller 110 or stimulation device 105, the first and second stimulation electrodes 120 can stimulate their associated muscle or muscles simultaneously, or after a delay period defined with respect to each other or with respect to the induced heart compression. In these examples, blood forced toward the heart as part of the venous blood flow during a first muscle's contraction can be further forced toward the heart by a subsequent contraction of a second muscle that is located along the venous return flow between the first muscle and the chest cavity.

In one embodiment, a first pair of stimulation electrodes 120 stimulates a first muscle located in a limb of the subject and another pair of stimulation electrodes 120 stimulates a second muscle located in the subject's abdomen. In this example, the second abdominal muscle is located between the first limb muscle and the subject's heart, and along or proximate to the venous return blood flow path. Sequential stimulation by the different pairs of stimulations electrodes 120 of the first muscle and then the second muscle pushes the blood along the venous return blood flow path from the first muscle and past the second muscle toward the subject's heart, where it is eventually pushed into the thoracic cavity. The second muscle in this example can be any abdominal muscle. In one embodiment, the second muscle is located in the lower portion of the abdomen, where it is, for example, outside of the chest cavity and distal from the subject's heart.

It should be appreciated that in some embodiments, additional pairs of stimulation electrodes 120 may can be provided. For example, additional stimulation electrodes 120 can be provided to stimulate muscles between the first muscle located in the subject's limb, and the second muscle located in the lower portion of the subject's abdomen. Such additional stimulation electrodes 120 may be used to push the venous blood from one muscle to another and ultimately toward the subject's heart.

In one embodiment, stimulation electrode 120 stimulates muscle contraction to expel blood from the muscle, e.g., to force the blood further along the venous blood portion of the circulatory system toward the chest cavity. This enhances blood entry into the chest cavity, including the heart, during the negative thoracic pressure period that occurs during the heart relaxation or chest cavity expansion phase of cardiopulmonary resuscitation. While venous blood is drawn into the chest cavity during the expansion phase, stimulation electrode 120 may induce muscle contraction during both the heart compression phase and the heart relaxation phase. As noted above, in one embodiment, signals are received indicating 70-110 induced heart compressions per minute, with stimulation electrode 120 stimulating muscle contraction at a rate of one to five times per minute. Current passing from stimulation electrode 120 to, for example, the leg muscle pushes blood from that leg muscle toward the heart in the venous blood flow. Upon expulsion from the leg muscle, the expelled blood generally is proximate the leg muscle in the venous blood flow. At this time the blood remains distal to the heart, e.g., still generally within or proximate to the leg and outside of the subject's chest cavity and abdomen and one or more compression/relaxation cycles away from being drawn into the chest cavity during the relaxation phase. Accordingly, while in one embodiment some blood is drawn into the chest cavity during the heart's relaxation phase (and accompanying chest expansion), blood may be expelled toward the heart from a muscle distal to the heart during either the relaxation phase or the heart compression phase (e.g., during chest compression) where it will eventually be drawn into the chest cavity during a subsequent heart relaxation phase.

The volume of blood that flows through the muscle toward the chest cavity during stimulation electrode induced contraction varies based on the size and health of the subject. In one embodiment, stimulation of larger muscles or muscle groups, such as the calf muscle group, increases venous blood flow by about 20-35%. For example, when the calf is induced to contract by stimulation electrode 120, blood may be expelled through the muscle toward the chest cavity at a flow rate of between 9 and 43 cm/sec. This flow rate varies based on a variety of factors, such as which muscle is induced to contract, the rate of contraction, the size of the muscle, and the size of the subject, for example. In one embodiment, different amounts of blood are expelled from the muscle toward the heart responsive to stimulation electrode 120 inducing the muscle to contract due to muscle fatigue. For example, calf muscles may have a lower fatigue rate than respiratory muscles, making them better suited for electrical stimulation.

Figure 3:
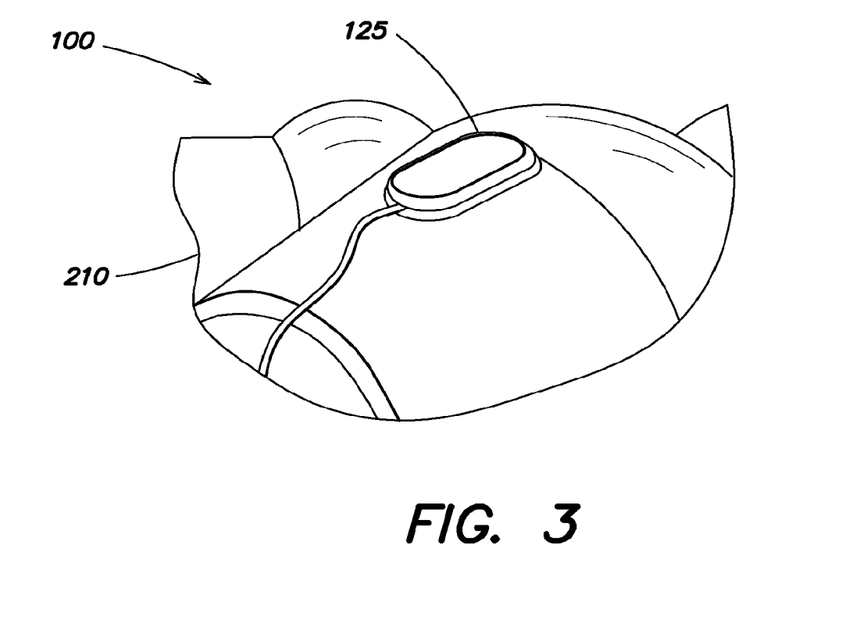
FIG. 3 is a partial perspective view of a cardiopulmonary resuscitation device in accordance with an embodiment.

FIG. 3 is a partial perspective view depicting cardiopulmonary resuscitation device 125 in accordance with one embodiment. In one embodiment, cardiopulmonary resuscitation device 125 is placed on the subject's chest cavity to facilitate cardiopulmonary resuscitation by providing to a rescuer information regarding chest compressions, such as force, compression depth, or timing information, as well as feedback information indicating that a previous chest compression was or was not acceptable based on its depth, rate, speed, or applied force.

In one embodiment, cardiopulmonary resuscitation device 125 is a real time CPR feedback device such as the PocketCPR® device manufactured by Zoll Medical Corporation of Chelmsford Mass., that provides real time audio or visual feedback information about the rate and depth of chest compressions. For example, the real time CPR feedback device can be placed on the subject's chest, and the rescuer places his or her hands on top of the device and follows prompts to execute chest compressions. In one embodiment, the calf (or other) muscle stimulation is synchronized with the real time CPR feedback device information. For example, controller 110 can synchronize induced heart compressions caused by the chest compression with the rate or depth information about the chest compressions.

In one embodiment, cardiopulmonary resuscitation device 125 includes at least one sensor such as an accelerometer or force sensor capable of sensing induced chest compressions as well as information about their rate and depth. Cardiopulmonary resuscitation device 125 may, but need not, include other sensors to sense information about the subject's health, e.g., a sensor for detecting ventricular fibrillation, a pulse or oxygen sensor, etc. In this embodiment, with controller 110 or other logic devices, cardiopulmonary resuscitation device 125 indicates to a rescuer when to begin resuscitation efforts.

In some situations, a rescuer aiding the subject may not have the time, medical training, or medical equipment necessary to monitor other information concerning the subject's health. In one embodiment, system 100 stimulates muscle contraction based solely on the information indicative of the induced heart compression, without any other electrical measurements of the subject's heart, and in the absence of any other information concerning the subject's health.

In some embodiments, cardiopulmonary resuscitation device 125 mechanically induces a heart compression, either directly (e.g., a chest compression device that physically compresses the subject's chest) or by instructions conveyed to a rescuer who induces heart compression via manual chest compressions. In one embodiment, cardiopulmonary resuscitation device 125 mechanically induces a heart compression when the subject appears to be in distress but without determining whether or not the subject has any residual myocardial function, such as pulseless electrical activity, electromechanical disassociation, electrical cardiac activity, or other residual cardiac electrical or mechanical activity. In this illustrative embodiment, the rescuer compresses the subject's chest to induce heart compressions without the aid of equipment to sense electrical or mechanical heart activity, and does not know whether the subject is experiencing any pulseless electrical activity. This is in contrast to synchronizing chest compressions with the heart's residual mechanical function or any measured electrical cardiac activity, such as the chest compression technique of U.S. Pat. No. 7,645,247, which synchronizes chest compressions with detected pulseless electrical activity.

In other embodiments, cardiopulmonary resuscitation device 125 may be placed in other locations distal to the subject's chest cavity, and in still other embodiments, cardiopulmonary resuscitation device 125 need not be placed on the subject at all. In some embodiments, cardiopulmonary resuscitation device 125 is an internal device completely or partially implanted in the subject. In some embodiments, cardiopulmonary resuscitation device 125 can use audio or visual signals to prompt a rescuer to manually induce chest compressions, and in other embodiments can induce chest compressions by applying drugs or electric current to the chest cavity. In one embodiment, cardiopulmonary resuscitation device 125 is part of an automatic external defibrillator or pacing device such as the M Series® or R Series® defibrillator devices manufactured by the Zoll Medical Corporation of Chelmsford Mass.

FIGS. 4-7 illustrate various perspective views of system 100 to enhance circulation in accordance with various embodiments, with the subject generally depicted during resuscitation efforts using system 100 while experiencing a condition such as ventricular fibrillation, an asystolic condition, or cardiac arrest. With respect to FIG. 4, stimulation device 105 is communicatively coupled by wires to cardiopulmonary resuscitation device 125 and to stimulation electrodes 120. In some embodiments, stimulation device 125 and stimulation electrodes 120 are part of a non-invasive transcutaneous electrical nerve stimulation unit that applies electrical current through the skin to induce muscle contractions. In another embodiment, stimulation device 105 is part of a pacing device.

In one embodiment, at least one housing 205 that includes at least one stimulation electrode 120 is disposed on the subject at a location distal to the heart. For example, although illustrated proximal to the calf muscle in FIGS. 4-7, housing 205 can be configured for placement on any extremity of a subject, such as the arms, legs, hands, feet, or shoulders to stimulate muscles located outside the chest cavity and abdomen of the subject. In one embodiment, the housing 205 is dimensioned to fit about larger muscles, e.g., calf, thigh, bicep, or tricep muscles that generally are filled with more blood than smaller muscles like those found in the hands or feet. Contraction of these larger muscles that are located distal to the heart and distal to the chest cavity and abdomen of the subject can force more blood toward the subject's heart. Contracting muscles located outside the chest cavity enhances venous blood flow toward the heart and avoids interference with negative thoracic pressure blood drawn into the chest cavity during the heart relaxation phase. For example, stimulation of certain chest cavity or abdominal muscles such as the diaphragm could cause a chest or lung contraction that conflicts with cardiopulmonary resuscitation device 125 instructions regarding the timing of chest compressions, and can disrupt the heart/chest compression and relaxation cycle.

In some embodiments, such as those depicted in FIGS. 4-7, stimulation electrodes 120 may be activated simultaneously or at different times to stimulate their respective calf (or other) muscles and force blood from the muscles toward the heart. In other embodiments, stimulation electrodes 120 can be located on different body parts to stimulate different muscles together or separately to enhance venous blood flow toward the heart.

Figure 4:
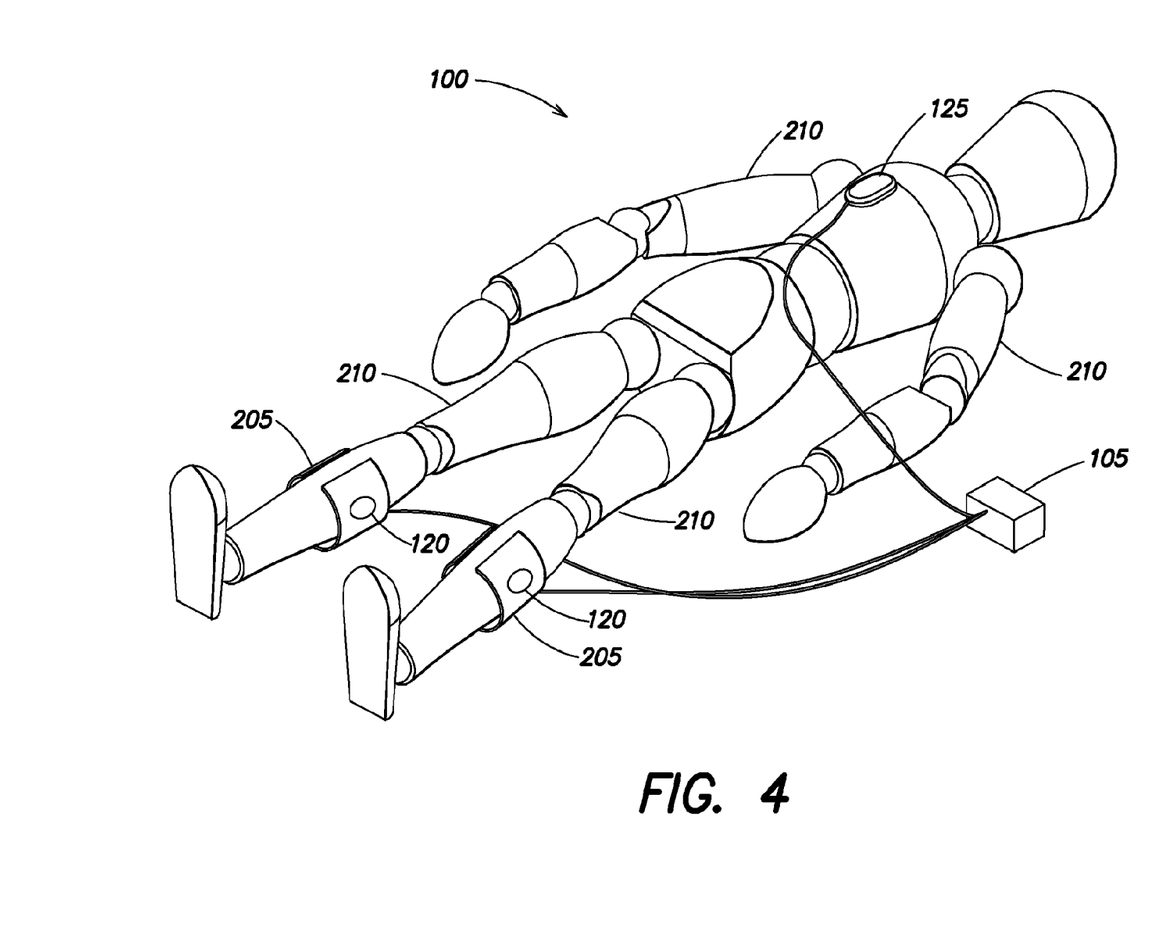
FIG. 4 is a perspective view of a system to enhance circulation in accordance with an embodiment.
Figure 5:
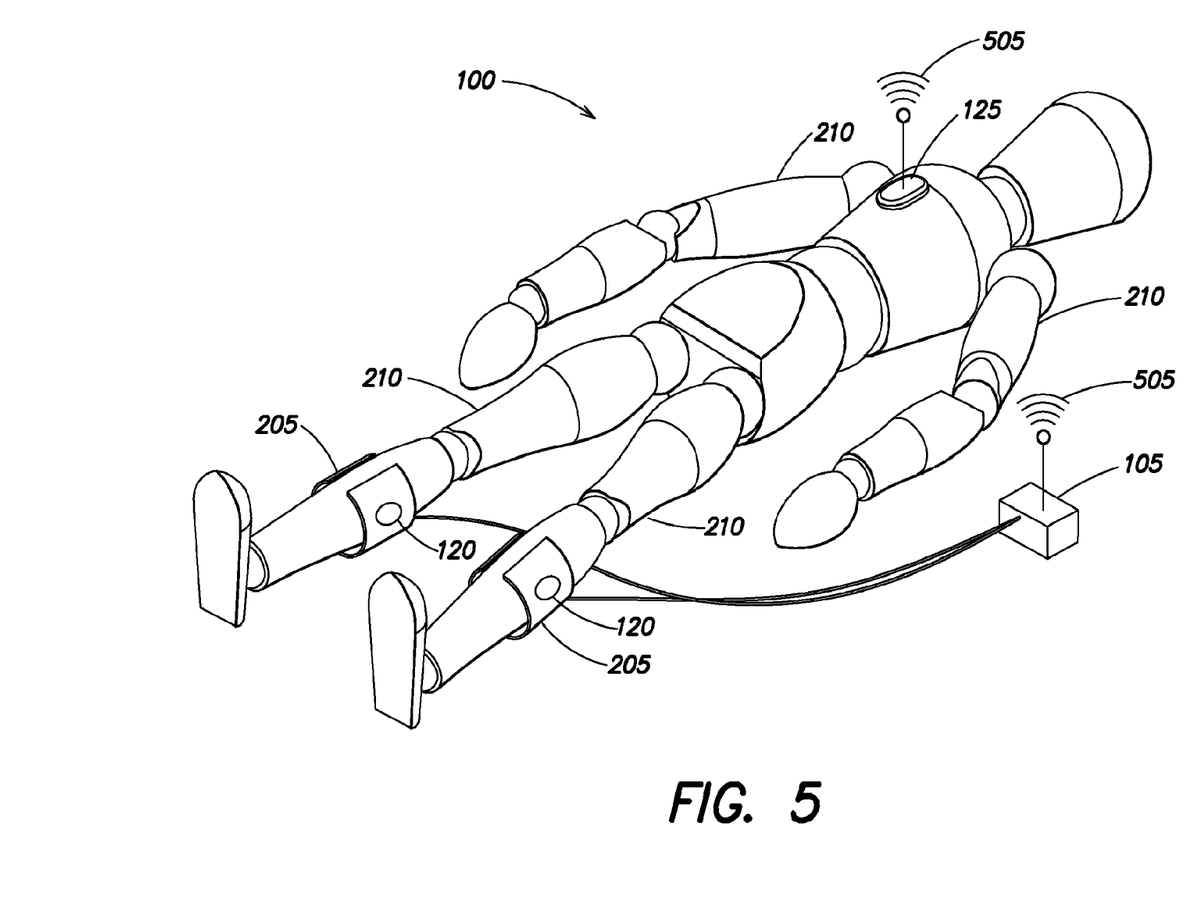
FIG. 5 is a perspective view of a system to enhance circulation in accordance with another embodiment.

FIG. 5 depicts an embodiment of system 100 where certain wired connections of FIG. 4 are replaced with wireless communications. As illustrated in FIG. 5, wireless interfaces 505 communicate information between stimulation device 105 and cardiopulmonary resuscitation device 125. With respect to FIGS. 1 and 5, stimulation device 105 and cardiopulmonary resuscitation device 125 may each have their own individual power sources 115, and each has at least some individual control logic.

Figure 6:
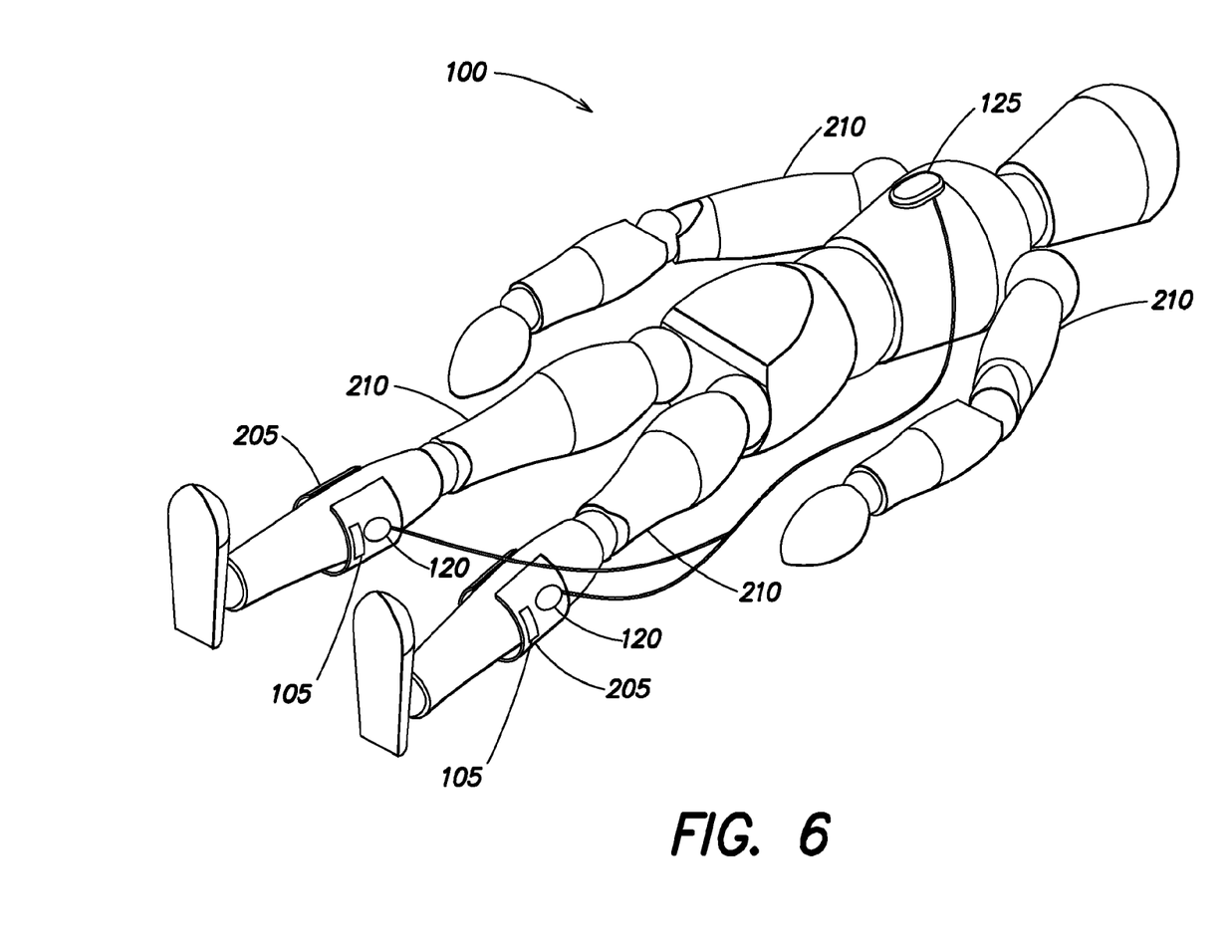
FIG. 6 is a perspective view of a system to enhance circulation in accordance with yet another embodiment.

FIG. 6 depicts an embodiment where the power and control aspects of stimulation device 105, e.g., controller 110 and power source 115, are integrated with stimulation electrodes 120. Stimulation device 105 may be disposed on the housing 205 that includes the stimulation electrodes 120. In some embodiments, portions of stimulation device 105 can be distributed. For example, cardiopulmonary resuscitation device 125 may include a controller that controls operation of stimulation device 105.

Figure 7:
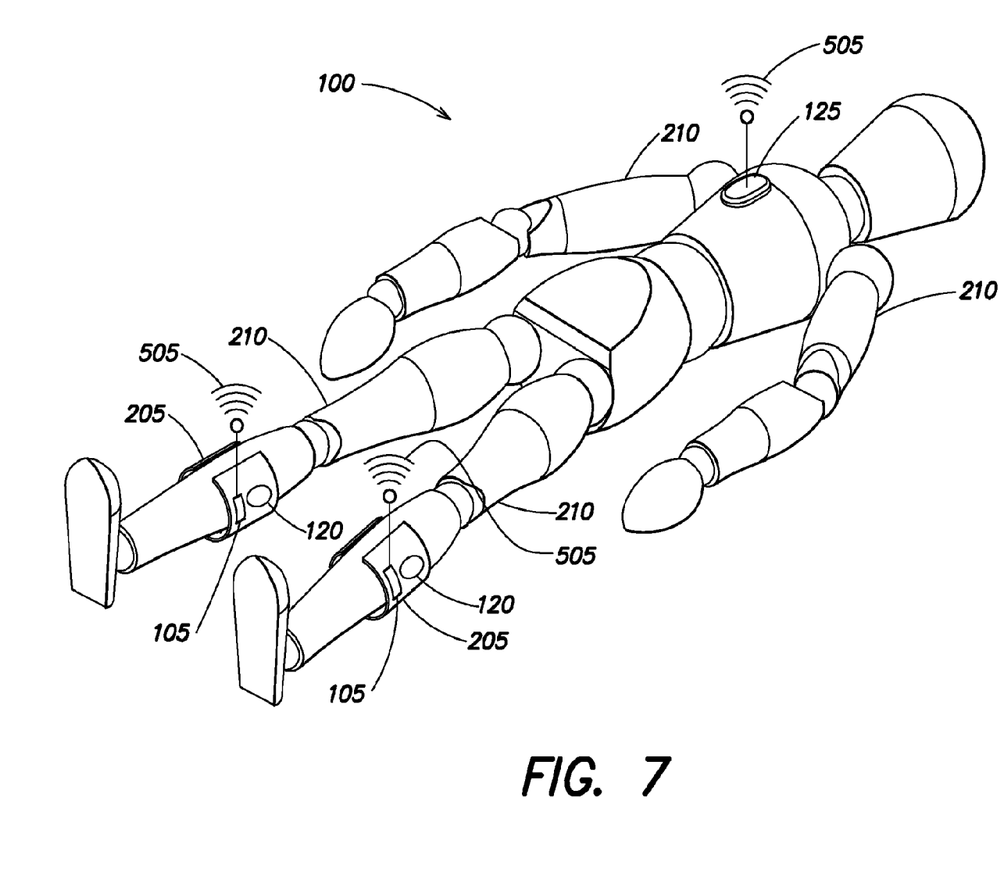
FIG. 7 is a perspective view of a system to enhance circulation in accordance with a further embodiment.

FIG. 7 depicts an embodiment of system 100 having wireless communication between stimulation device 105 and cardiopulmonary resuscitation device 125 via wireless interfaces 505, and where each housing 205 includes a stimulation device 105 integrated with housing 205. Any information or communication discussed herein can be communicated in a wired or wireless fashion between stimulation device 105, cardiopulmonary resuscitation device 125, and stimulation electrodes 120.

As illustrated in the embodiments depicted in FIGS. 4-7, stimulation electrodes 120 are applied to each of the subject's legs, generally proximate to the calf muscle. Stimulation electrodes 120 are connected to stimulation device 105, which may include a pacing device or a transcutaneous electrical nerve stimulation unit. This connection may be wired, wireless or both, and stimulation device 105 may be a separate unit, or distributed and integrated into the at least one housing 205 or the cardiopulmonary resuscitation device 125. In one embodiment, information is provided electronically from cardiopulmonary resuscitation device 125 to stimulation device 105 (in a wired, wireless, or hybrid manner) to synchronize calf (or other) muscle stimulation associated with stimulation electrodes 120 with heart compressions and chest compressions associated with cardiopulmonary resuscitation device 125. For example, synchronized calf muscle contractions can be induced to occur during maximum chest compression, e.g., at the bottom of the down-stroke chest compression. This complements venous blood flow due to negative thoracic pressure during the heart relaxation and chest expansion cycle that occurs after the down-stroke chest compression. Other synchronizations are possible, and distal muscle stimulation need not occur in a 1:1 ratio with heart compressions. For example, distal muscle contraction can be synchronized to occur at the bottom of the down-stroke chest compression at ratios between 1:5 and 1:20 with respect to induced heart compressions, as well as other ratios within and beyond these ranges.

Synchronized distal muscle contractions can be induced at other points during heart compression and relaxation (chest compression and expansion) cycles. For example, induced distal muscle contractions can be timed to occur prior to the bottom of the down-stroke chest compression, during chest compression, during heart compression, subsequent to the bottom of the down-stroke compression, during heart relaxation, during chest expansion, at the top of up-stroke expansion, when the heart is fully relaxed, or when the chest is fully expanded.

In one embodiment, heart compressions and distal muscle contractions are not synchronized. For example, stimulation device 105 may prompt stimulation electrodes 120 to induce muscle contraction at a fixed rate, such as between one and five times per minute, regardless of the phase of heart and chest compressions and expansions induced by cardiopulmonary resuscitation device.

Figure 8:
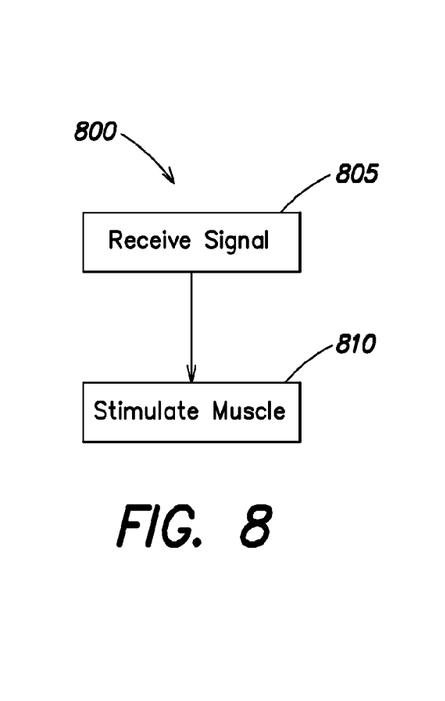
FIG. 8 is a flow chart depicting a method of enhancing circulation in accordance with an embodiment.

FIG. 8 is a flow chart depicting a method of enhancing circulation in a subject. In one embodiment, method 800 includes an act of receiving at least one signal (ACT 805). For example, the received signal may include a signal responsive to an induced heart compression applied to the subject during cardiac events such as ventricular fibrillation, an asystolic condition, or sudden cardiac arrest (ACT 805). In one embodiment, receiving the signal (ACT 805) includes receiving an induced chest compression signal, such as a signal indicative of a down-stroke chest compression. Receiving the signal (ACT 805) may also include receiving information based on the rate, depth, and velocity of an induced chest compression applied to a subject during ventricular fibrillation, an asystolic condition, or sudden cardiac arrest. In one embodiment, receiving the signal (ACT 805) includes receiving the signal at a stimulation device that is coupled with a stimulation electrode configured to induce stimulation of a muscle that is located distal to the subject's heart and outside the subject's chest cavity and abdomen. In some embodiments, receiving the signal (ACT 805) includes receiving the signal from a cardiopulmonary resuscitation device. In one embodiment, the signal is received (ACT 805) at a rate of 70-110 times per minute. Receiving a signal (ACT 805) may also include receiving a plurality of signals, each signal indicative of an induced heart compression associated with a chest compression.

Method 800 also includes an act of stimulating at least one muscle (ACT 810). Stimulating the muscle (ACT 810) includes, in one embodiment, applying electrical current to an external surface of the subject in the vicinity of the muscle targeted for contraction. For example, stimulating the muscle (ACT 810) may include transcutaneous electrical nerve stimulation that applies current to the muscle via stimulation electrodes in contact with the subject's skin generally proximate to the muscle. Barriers such as clothes, gels, or other material may be present between the electrodes and the skin. When, for example, permeable non-conductive barriers such as clothes are present they may either be removed, or a coupling agent such as a liquid gel or saline solution can be applied to the barrier to conduct the current through the barrier to stimulate the muscle. In one embodiment, non-permeable, non-conductive barriers are removed prior to stimulating the muscle.

In one embodiment, stimulating the muscle (ACT 810) occurs responsive to the act of receiving the signal (ACT 805). The muscle, for example, may be a muscle located distal to the subject's chest cavity and abdomen, such a leg, arm, shoulder, hand, or foot muscle. In one embodiment, the muscle is electrically stimulated to contract (ACT 810) and increase venous blood flow toward the subject's heart.

In one embodiment, stimulating the muscle (ACT 810) expels blood through the muscle and toward the chest cavity during a compression phase of the heart muscle. This may occur, for example, during chest compressions associated with induced heart compressions. In some embodiments, stimulating the muscle (ACT 810) expels blood through the muscle in the venous blood flow toward the chest cavity during a relaxation phase of the heart muscle. This may occur, for example, subsequent to an induced heart compression during chest expansion and when the venous blood flow is subject to negative thoracic pressure. In one embodiment, the muscle is stimulated (ACT 810) to contract at a rate of one to five times per minute.

In one embodiment, stimulating the muscle (ACT 810) can include stimulating a first portion of a muscle group to contract with a first electrode, and stimulating a second portion of the muscle group to contract with a second electrode. These multiple stimulations can be responsive to the received signal (ACT 805) and can be consecutive or concurrent. The different portions of the muscle group can be different muscles of the same muscle group, (e.g., different muscles that constitute the calf of one leg), or different portions of the same muscle. The first and second portions of a muscle group can be stimulated responsive the same received signal indicative of one induced heart compression, or responsive to different signals received at different times and associated with different induced heart compression. In one embodiment, the muscle is stimulated to contract when it is determined that the muscle is engorged with a sufficient, e.g., threshold, amount of blood. This determination may be aided by the use of a sensor capable of detecting this state, or may be based on a time period from a previous stimulation or contraction.

Figure 9:
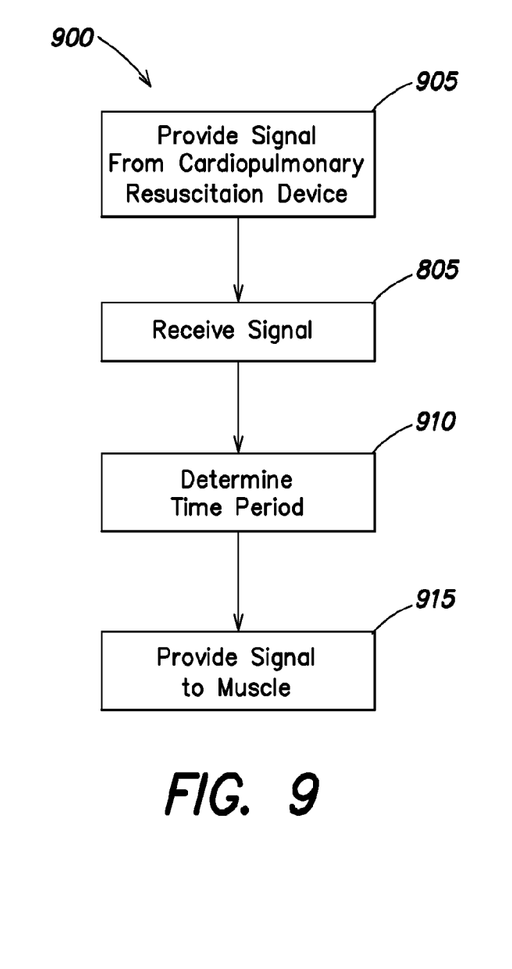
FIG. 9 is a flow chart depicting a method of enhancing circulation in accordance with another embodiment.

FIG. 9 is a flow chart depicting a method of enhancing circulation in a subject by, for example, synchronizing induced heart compression with induced muscle contractions of a muscle distal to the subject's heart. In one embodiment, method 900 includes the act of providing a signal (ACT 905). The signal may be provided by a cardiopulmonary resuscitation device configured for placement on the subject's chest cavity, and may indicate an induced heart compression. The signal may be responsive to an induced heart compression applied to the subject during ventricular fibrillation, an asystolic condition, or sudden cardiac arrest, and can indicate a down-stroke chest compression. The signal that is provided (ACT 905) may include information based on the rate, depth, and velocity of an induced chest compression applied to a subject during any of ventricular fibrillation, an asystolic condition, or sudden cardiac arrest.

In one embodiment, method 900 includes an act of receiving a signal, as described above with respect to FIG. 8, indicating that the heart has been compressed, or initiated compression (ACT 805). In one embodiment, the signal provided in ACT 905 by the cardiopulmonary resuscitation device is received by the stimulation device. Method 900 may also include an act of determining a time period (ACT 910). For example, based at least in part on the received signal (ACT 805), a time period to stimulate the muscle can be determined (ACT 910). Determining when to stimulate the muscle (ACT 910) can include determining to stimulate the muscle periodically, e.g., at a ratio between one to five muscle stimulations for every 20 induced heart compressions. In one embodiment, determining when to stimulate the muscle (ACT 910) includes determining a delay period that begins during an induced heart compression, and where the distal muscle is to be stimulated upon expiration of the delay period. In one embodiment, the time period is determined based on the induced heart compression. For example, the determined time period (ACT 910) may be a time period that coincides with the maximum heart compression (e.g., bottom of the compression down-stroke) or any other point of the heart compression-relaxation or chest compression-expansion cycle. In one embodiment, determining the time period includes determining when the muscle, e.g., leg or arm muscle is engorged with a threshold amount of blood.

Method 900 may also include the act of providing a signal to the muscle to initiate contraction of the muscle (ACT 915). In one embodiment, the signal provided to the muscle includes an electrical current provided to a stimulation electrode placed on the subject proximate to the muscle. The current is applied to the subject to induce muscle contraction at a determined time. This muscle contraction expels blood from the muscle toward the subject's chest cavity. While the expelled blood generally enters the chest cavity during a chest expansion phase, the blood can be expelled from the muscle toward the chest cavity due to muscle contraction that occurs during either the compression or expansion phases.

Figure 10:
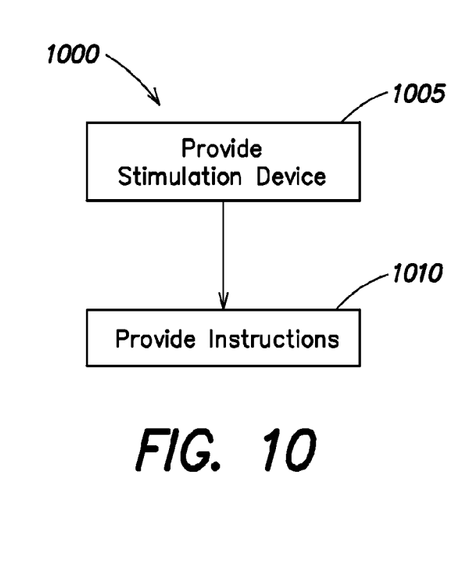
FIG. 10 is a flow chart depicting a method of enhancing circulation in accordance with yet another embodiment.

FIG. 10 is a flow chart depicting a method of enhancing circulation. In one embodiment, the method includes providing at least one stimulation device (ACT 1005). The provided stimulation device enhances circulation of a subject, and the act of providing may include providing a stimulation device that includes at least one stimulation electrode configured for placement on at least one of the subject's limbs. Providing the stimulation device (ACT 1005) may also include providing a stimulation device having at least one controller that can communicate with the at least one stimulation electrode, and that can receive signals indicative of induced heart compressions. In one embodiment, this controller provides signals to the at least one stimulation electrode to induce contraction of a muscle distal to the subject's heart.

In one embodiment, providing the stimulation device (ACT 1005) includes providing the stimulation device to a rescuer. The provided stimulation device may also communicate with at least one pacing unit or automatic defibrillator device, such as the M Series® or R Series® defibrillator devices manufactured by the Zoll Medical Corporation, of Chelmsford, Mass.

In one embodiment, method 1000 further includes an act of providing instructions (ACT 1010). The act of providing instructions may include providing written instructions together with the stimulation device. The instructions generally indicate how to operate the stimulation device during a rescue attempt. For example, providing instructions (ACT 1010) may include directing the rescuer to place the stimulation electrode on the subject's limb. In some embodiments, instructions may be provided in any combination of written form using labels or an instruction booklet or pamphlet, audible form using audible commands given by the stimulation device, or in visual form using a text or graphical display. In one embodiment, providing instructions (ACT 1010) includes instructing the user how to arrange the stimulation device or stimulation electrode on or about the patient when the patient is experiencing ventricular fibrillation, an asystolic condition, or cardiac arrest.

Having now described some illustrative embodiments, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed only in connection with one embodiment are not intended to be excluded from a similar role in other embodiments.

Note that in FIGS. 1 through 10, the enumerated items are shown as individual elements. In actual implementations of the systems and methods described herein, however, they may be inseparable components of other electronic devices such as a digital computer. Thus, actions described above may be implemented at least in part in software that may be embodied in an article of manufacture that includes a program storage medium. The program storage medium may include any form of computer readable media, such as a computer disk (e.g., magnetic or optical), non-volatile memory (e.g., ROM or PROM), volatile memory, (RAM), tape, etc. The program storage medium can include at least non-transient mediums, and the signals can include at least non-transient signals.

From the foregoing, it will be appreciated that the systems and methods described herein provide a simple and effective way to supplement venous blood flow toward the heart during any cardiac event such as ventricular fibrillation, an asystolic condition, or sudden cardiac arrest. These systems and methods increase the volume of blood pumped through the heart during resuscitation efforts. This increases blood oxygenization and distribution of oxygenated blood to the body's organs and tissues during cardiopulmonary resuscitation.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment in any manner consistent with the aspects and embodiments disclosed herein.

One skilled in the art will realize the systems and methods described herein may be embodied in other specific forms. For example, the stimulation device need not be a separate unit, and the subject need not be experiencing complete cardiac arrest. The foregoing embodiments are therefore to be considered in all respects illustrative rather than limiting of the described systems and methods. Scope of the systems and methods described herein is thus indicated by the appended claims, rather than the foregoing description, and all changes that come within the meaning and range of equivalency of the claims are therefore intended to be embraced therein.

What is claimed is:

1. A stimulation device to enhance cardiopulmonary circulation, comprising:
    a stimulation electrode configured for placement onto a limb of the subject; and
    a controller, communicatively coupled with the stimulation electrode, the controller being configured to receive a signal indicative of an induced heart compression applied to a heart of the subject, and responsive to receipt of the signal, to direct the stimulation electrode to induce contraction of a muscle in the limb of the subject to force blood from the muscle and into a venous blood flow toward the heart in the absence of an inflatable therapeutic device.

2. The stimulation device of claim 1, wherein the controller is further configured to:
    identify a time period that begins during the induced heart compression; and
    direct the stimulation electrode to induce contraction of the muscle upon expiration of the time period.

3. The stimulation device of claim 2, wherein the controller is further configured to receive the signal from a cardiopulmonary resuscitation device.

4. The stimulation device of claim 3, wherein the cardiopulmonary resuscitation device includes a power source, and wherein the stimulation device is powered by the power source of the cardiopulmonary resuscitation device.

5. A stimulation device to enhance cardiopulmonary circulation, comprising:
a stimulation electrode configured for placement onto a limb of the subject; and a controller, communicatively coupled with the stimulation electrode, the controller being configured to receive a signal indicative of an induced heart compression applied to a heart of the subject, and responsive to receipt of the signal, to direct the stimulation electrode to induce contraction of a muscle in the limb of the subject to force blood from the muscle and into a venous blood flow toward the heart, wherein the controller is further configured to determine an amount of blood present in the muscle and to direct the stimulation electrode to induce contraction of the muscle when the amount of blood present in the muscle is at least a threshold amount of blood.

6. A stimulation device to enhance cardiopulmonary circulation, comprising:
a stimulation electrode configured for placement onto a limb of the subject; and a controller, communicatively coupled with the stimulation electrode, the controller being configured to receive a signal indicative of an induced heart compression applied to a heart of the subject, and responsive to receipt of the signal, to direct the stimulation electrode to induce contraction of a muscle in the limb of the subject to force blood from the muscle and into a venous blood flow toward the heart, wherein the controller is further configured to receive the signal at a rate of 70 to 110 times per minute and to direct the stimulation electrode to induce contraction of the muscle at a rate of one to five times per minute.

7. The stimulation device of claim 6, wherein the stimulation electrode is disposed in a housing having an incomplete cylinder shape.

8. The stimulation device of claim 7, wherein the stimulation electrode further comprises a conductive plate affixed to an inner surface of the housing.

9. The stimulation device of claim 1, wherein the controller is configured to issue an instruction to mechanically induce the induced heart compression or to manually induce the induced heart compression.

10. The stimulation device of claim 1, wherein the controller is further configured to direct the stimulation electrode to induce contraction of the muscle during a compression phase of the heart.

11. The stimulation device of claim 1, wherein the controller is further configured to direct the stimulation electrode to induce contraction of the muscle during a relaxation phase of the heart.

12. A method of enhancing cardiopulmonary circulation in a subject, comprising acts of:
receiving a signal responsive to an induced heart compression applied to the subject; and
electrically stimulating, responsive to receipt of the signal, a muscle that is located distal to a chest cavity and abdomen of the subject to contract and increase venous blood flow toward a heart of the subject in the absence of an inflatable therapeutic device.

13. The method of claim 12, wherein the act of receiving includes receiving the signal from a cardiopulmonary resuscitation device having a power source, and wherein the act of electrically stimulating includes electrically stimulating the muscle using energy drawn from the power source of the cardiopulmonary resuscitation device.

14. The method of claim 13, further comprising an act of:
determining a time period responsive to receipt of the signal;
wherein the act of electrically stimulating includes electrically stimulating the muscle subsequent to expiration of the time period.

15. A method of enhancing cardiopulmonary circulation in a subject, comprising acts of:
receiving a signal responsive to an induced heart compression applied to the subject; electrically stimulating, responsive to receipt of the signal, a muscle that is located distal to a chest cavity and abdomen of the subject to contract and increase venous blood flow toward a heart of the subject; and
determining whether the muscle is engorged with a threshold amount of blood;
wherein the act of electrically stimulating includes electrically stimulating the muscle in response to a determination that the muscle is engorged with the threshold amount of blood.

16. The method of claim 15, further comprising an act of:
inducing the induced heart compression in an absence of electrical measurements of the heart of the subject.

17. The method of claim 15, further comprising an act of:
inducing the induced heart compression in an absence any information about pulseless electrical activity of the subject.

18. A method of enhancing cardiopulmonary circulation in a subject, comprising acts of:
receiving a signal responsive to an induced heart compression applied to the subject; electrically stimulating, responsive to receipt of the signal, a muscle that is located distal to a chest cavity and abdomen of the subject to contract and increase venous blood flow toward a heart of the subject;
inducing the induced heart compression responsive to a prompt received from a cardiopulmonary resuscitation feedback device;
wherein the act of receiving the signal includes receiving, from the cardiopulmonary resuscitation feedback device, the signal identifying at least one of a rate of chest compression and a depth of chest compression; and
wherein the act of electrically stimulating includes synchronizing the act of electrically stimulating the muscle with the signal identifying the at least one of the rate of chest compression and the depth of chest compression.

19. The method of claim 18, wherein the act of receiving the signal includes receiving the signal at a rate of 70 to 110 times per minute, and wherein the act of electrically stimulating includes electrically stimulating the muscle at a rate of one to five times per minute.

20. The method of claim 19, wherein the act of receiving includes receiving the signal during at least one of ventricular fibrillation, an asystolic condition, and cardiac arrest.

21. The method of claim 19, wherein the act of receiving includes receiving the signal during an arrhythmic cardiac event.

22. The method of claim 13, wherein the act of electrically stimulating includes expelling blood from the muscle into the venous blood flow toward the chest cavity during a relaxation phase of the heart of the subject subsequent to the induced heart compression.

23. The method of claim 13, wherein the act of electrically stimulating includes expelling blood from the muscle into the venous blood flow toward the chest cavity during a compression phase of the heart of the subject.

24. The method of claim 13, wherein the act of electrically stimulating includes electrically stimulating at least one of a leg muscle and an arm muscle of the subject.

25. The method of claim 13, wherein the act of electrically stimulating includes electrically stimulating a first portion of the muscle to contract at a first time, and electrically stimulating a second portion of the muscle to contract at a second time.

26. The method of claim 13, wherein the muscle is a first muscle, and wherein the act of electrically stimulating includes electrically stimulating the first muscle to contract at a first time; the method further comprising an act of electrically stimulating a second muscle to contract at a second time.

27. The method of claim 12, further comprising an act of: mechanically inducing the induced heart compression.

28. The method of claim 12, further comprising an act of: issuing an instruction to manually induce the induced heart compression.

29. A method of facilitating care of a subject, comprising:
providing a stimulation device to enhance cardiopulmonary circulation in a subject in the absence of an inflatable therapeutic device, the stimulation device including a stimulation electrode configured for placement onto a limb of the subject and a controller communicatively coupled to the stimulation electrode, the controller being configured to receive a signal indicative of an induced heart compression applied to a heart of the subject, and responsive to receipt of the signal, to direct the stimulation electrode to induce contraction of a muscle in the limb of the subject to force blood from the muscle and into a venous blood flow toward the heart.

30. The method of claim 29, further comprising:
providing instructions to operate the stimulation device, the instructions including at least one instruction directing a user to place the stimulation electrode on the limb of the subject.

* * * * *